United States Patent
Niinistö et al.

(10) Patent No.: US 9,460,581 B2
(45) Date of Patent: Oct. 4, 2016

(54) MEDICATION DISPENSER AND METHOD FOR DISPENSING MEDICATIONS

(71) Applicant: EVONDOS OY, Salo (FI)

(72) Inventors: Jyrki Niinistö, Halikko (FI); Mika Apell, Turku (FI)

(73) Assignee: EVONDOS OY, Salo (FI)

( * ) Notice: Subject to any disclaimer, the term of this patent is extended or adjusted under 35 U.S.C. 154(b) by 146 days.

(21) Appl. No.: 14/102,015

(22) Filed: Dec. 10, 2013

(65) Prior Publication Data

US 2014/0158703 A1 Jun. 12, 2014

(30) Foreign Application Priority Data

Dec. 10, 2012 (EP) .................................... 12196283

(51) Int. Cl.
*G07F 11/42* (2006.01)
*A61J 7/04* (2006.01)
*G06F 19/00* (2011.01)
*B65D 83/04* (2006.01)

(52) U.S. Cl.
CPC .............. *G07F 11/42* (2013.01); *A61J 7/0409* (2013.01); *G06F 19/3462* (2013.01); *A61J 2200/30* (2013.01); *B65D 83/0445* (2013.01)

(58) Field of Classification Search
CPC ........ G07F 11/42; G07F 11/58; G07F 11/66; G07F 17/0092; G07F 19/3462
See application file for complete search history.

(56) References Cited

U.S. PATENT DOCUMENTS

| | | | |
|---|---|---|---|
| 4,903,953 A * | 2/1990 | Winkler ............. | G07D 11/0081 221/7 |
| 4,971,221 A | 11/1990 | Urquhart et al. | |
| 5,097,982 A | 3/1992 | Kedem et al. | |
| 5,513,773 A * | 5/1996 | Cargill ................... | B65H 5/062 221/231 |
| 5,805,051 A | 9/1998 | Herrmann et al. | |
| 6,529,446 B1 | 3/2003 | de la Huerga | |
| 7,264,136 B2 * | 9/2007 | Willoughby ........... | B65D 75/42 221/13 |
| 8,019,417 B2 | 9/2011 | Bornzin et al. | |
| 8,600,548 B2 * | 12/2013 | Bossi .................. | G06F 19/3462 700/231 |
| 2002/0027507 A1 | 3/2002 | Yarin et al. | |
| 2002/0067270 A1 | 6/2002 | Yarin et al. | |
| 2003/0099158 A1 | 5/2003 | De la Huerga | |

(Continued)

FOREIGN PATENT DOCUMENTS

| | | | |
|---|---|---|---|
| EP | 2 026 298 A1 | 2/2009 | |
| EP | 2 457 550 A1 | 5/2012 | |

(Continued)

*Primary Examiner* — Gene Crawford
*Assistant Examiner* — Kelvin L Randall, Jr.
(74) *Attorney, Agent, or Firm* — Buchanan Ingersoll & Rooney PC

(57) ABSTRACT

The present invention relates to a medication dispenser that comprises a first container for holding medication packages to be dispensed, and conveying means for conveying medication packages from the first container to an outlet of the medication dispenser, the conveying means comprising a first conveyor that is arranged in connection with the outlet and is capable of conveying a medication package in a first and a second conveying direction, so that a medication package can be conveyed to the outlet and retracted inside the medication dispenser. The first conveyor comprises two opposing belt conveyors between which a medication package is arranged to be conveyed, both of the belt conveyors comprising an endless belt and a plurality of rollers around which the endless belt is arranged. The invention also relates to a method for dispensing medications.

14 Claims, 2 Drawing Sheets

(56) References Cited

U.S. PATENT DOCUMENTS

| | | | |
|---|---|---|---|
| 2004/0117062 A1* | 6/2004 | Bonney | A61M 15/0043 700/237 |
| 2004/0149767 A1* | 8/2004 | Boehm | B65B 1/46 221/25 |
| 2004/0158350 A1* | 8/2004 | Ostergaard | A61J 7/0481 700/231 |
| 2005/0041531 A1 | 2/2005 | Sekura | |
| 2005/0240305 A1 | 10/2005 | Bogash et al. | |
| 2005/0268909 A1 | 12/2005 | Bonney et al. | |
| 2006/0071011 A1 | 4/2006 | Varvarelis et al. | |
| 2007/0000805 A1* | 1/2007 | Van Den Brink | G06K 9/00 206/531 |
| 2007/0043469 A1 | 2/2007 | Draper | |
| 2007/0185615 A1 | 8/2007 | Bossi et al. | |
| 2007/0260487 A1 | 11/2007 | Bartfeld et al. | |
| 2008/0059228 A1 | 3/2008 | Bossi et al. | |
| 2008/0104830 A1* | 5/2008 | Yuyama | B65C 1/02 29/791 |
| 2008/0119958 A1 | 5/2008 | Bear et al. | |
| 2008/0215289 A1 | 9/2008 | Sekura | |
| 2008/0290106 A1 | 11/2008 | van der Klaauw et al. | |
| 2009/0030730 A1 | 1/2009 | Dullemen et al. | |
| 2009/0198208 A1 | 8/2009 | Stavsky et al. | |
| 2009/0301946 A1* | 12/2009 | Razzaboni | G07D 11/0072 209/534 |
| 2010/0045466 A1 | 2/2010 | Sekura | |
| 2010/0127073 A1 | 5/2010 | van Esch | |
| 2010/0215231 A1 | 8/2010 | Bartfeld et al. | |
| 2010/0249997 A1 | 9/2010 | Greyshock et al. | |
| 2010/0305967 A1 | 12/2010 | Daya et al. | |
| 2011/0185565 A1* | 8/2011 | Yuyama | B65C 1/02 29/791 |
| 2011/0193705 A1 | 8/2011 | Sekura | |
| 2012/0004770 A1 | 1/2012 | Ooyen et al. | |
| 2012/0081225 A1 | 4/2012 | Waugh et al. | |
| 2012/0083666 A1 | 4/2012 | Waugh et al. | |
| 2012/0095592 A1* | 4/2012 | Yuyama | B65C 1/02 700/214 |
| 2012/0126958 A1 | 5/2012 | Kim et al. | |
| 2012/0199650 A1 | 8/2012 | Horst et al. | |
| 2012/0255967 A1* | 10/2012 | Hecht | A21B 3/07 221/150 A |
| 2012/0273087 A1 | 11/2012 | Stavsky et al. | |
| 2013/0169798 A1 | 7/2013 | Pellerin et al. | |
| 2014/0346017 A1* | 11/2014 | Hecht | A21B 3/07 198/890 |
| 2015/0058178 A1* | 2/2015 | Chirnomas | B65G 1/1373 705/27.1 |

FOREIGN PATENT DOCUMENTS

| | | |
|---|---|---|
| WO | 91/04726 A1 | 4/1991 |
| WO | 00/07538 A2 | 2/2000 |
| WO | 01/47466 A1 | 7/2001 |
| WO | 02/078593 A2 | 10/2002 |
| WO | 03/001337 A2 | 1/2003 |
| WO | 2007/129318 A2 | 11/2007 |
| WO | 2008/135823 A1 | 11/2008 |
| WO | 2009/095904 A1 | 8/2009 |
| WO | 2011/042840 A1 | 4/2011 |
| WO | 2011/112606 A1 | 9/2011 |
| WO | 2011/123931 A1 | 10/2011 |
| WO | 2011/123933 A1 | 10/2011 |
| WO | 2012/007411 A1 | 1/2012 |

* cited by examiner

MEDICATION DISPENSER AND METHOD FOR DISPENSING MEDICATIONS

TECHNICAL FIELD OF THE INVENTION

The present invention relates to a medication dispenser and to a method for dispensing medications according to the preambles of the appended independent claims.

BACKGROUND OF THE INVENTION

Various devices are used for assisting patients in complying with their medical regimens. The most sophisticated of these devices are so-called medication dispensers, which dispense to a patient proper dosages of medications at prescribed times. For the medication dispensers, the medications of a patient are typically prepackaged by licensed pharmacies into medication packages, which are connected together to form a strip.

In a conventional medication dispenser, medication packages are arranged to be delivered to a patient one package at a time according to the taking time information contained in a label of each medication package. The medication packages are conveyed from a container to an outlet of the medication dispenser with conveying means that comprises rollers for moving the medication packages. At the taking time of the medications, the medication dispenser notifies the patient. If the patient acknowledges the notification, the medication package is conveyed to the outlet of the medication dispenser. Otherwise, the medication package is kept in the medication dispenser.

Problems associated with known medication dispensers relate, due to the use of rollers, to the handling of medication packages. First, there is a risk of a medication package getting stuck inside the medication dispenser when the package is conveyed. A medication package may be driven out of the conveying path because the medication package has not been placed correctly into the container or is incorrectly aligned or bent while being conveyed. Second, there is a difficulty of moving a medication package in forward and backward directions, the feature of which is needed in some applications.

Other problems associated with known medication dispensers relate to defects in their medical safety. Once the patient has acknowledged the notification to take the medications, the medication package is delivered out of the medication dispenser without any further functionality to control the taking of the medications. It may thus happen that the patient forgets to take the medications right after he/she has acknowledged the notification. Furthermore, because the medication package remains available, there is a risk that the patient takes the medications after their correct taking time, or that the medications are accidentally taken by someone else than the patient.

OBJECTIVES OF THE INVENTION

It is the main objective of the present invention to reduce or even eliminate prior art problems presented above.

It is an objective of the present invention to provide a medication dispenser and a method for dispensing medications, which increase the medical safety compared to the prior art. In more detail, it is an objective of the invention to provide a medication dispenser that reduces or even eliminates the risk of a medication package getting stuck inside the medication dispenser. It is a further objective of the invention to provide a medication dispenser that allows a medication package to be moved in forward and backward directions easily and accurately.

It is also an objective of the invention to provide a method enabling to efficiently control the taking of medications. It is a further objective of the invention to provide a method enabling to reduce the probability of taking medications at a wrong time, or by someone else than the patient.

In order to realise the above-mentioned objectives, the medication dispenser and the method according to the invention are characterised by what is presented in the characterising parts of the appended independent claims. Advantageous embodiments of the invention are described in the dependent claims.

DESCRIPTION OF THE INVENTION

A typical medication dispenser according to the invention comprises a first container for holding medication packages to be dispensed, and conveying means for conveying medication packages from the first container to an outlet of the medication dispenser, the conveying means comprising a first conveyor arranged in connection with the outlet and being capable of conveying a medication package in a first and a second conveying direction, so that a medication package can be conveyed to the outlet and retracted inside the medication dispenser. In a typical medication dispenser according to the invention the first conveyor comprises two opposing belt conveyors between which a medication package is arranged to be conveyed, both of the belt conveyors comprising an endless belt and a plurality of rollers around which the endless belt is arranged.

The first conveyor is a bi-directional conveyor, which is capable of conveying a medication package in opposite directions. In the first conveying direction the medication package is conveyed towards the outlet, and in the second conveying direction the medication package is conveyed away from the outlet. When it is time to take the medications, the first conveyor conveys the medication package to the outlet and then, in a case where the patient has not taken the medication package from the outlet, retracts the medication package inside the medication dispenser. Preferably, the medication package is held with the first conveyor during the time the medication package is kept at the outlet.

The medication dispenser is arranged to dispense medication packages to provide the patient with the proper dosages of medications at prescribed times. The medication packages are conveyed with the conveying means from the first container to the outlet from which the patient can take the medication packages. The conveying means are driven by means of at least one actuator, such as an electric motor.

An electric motor can be arranged to drive one or more of the rollers via, for example, a belt or a gearwheel, and/or one or more of the rollers can have a built-in electric motor. A roller that is used for driving the endless belt is called a driving roller. At least one of the rollers of the first conveyor is a driving roller. Preferably, at least one of the rollers of both of the belt conveyors is a driving roller. For example, a roller of the first belt conveyor can have a built-in electric motor, to which a roller of the second belt conveyor is connected with a gearwheel. Depending on the direction on which the endless belts are rotated a medication package between them is conveyed either in a first or in a second conveying direction.

The first conveyor comprises two belt conveyors that are arranged opposite to each other so that a medication package may be conveyed between the endless belts of the belt conveyors. Each belt conveyor comprises an endless belt that is wound around the rollers. Preferably, the rollers of the belt conveyor are arranged in parallel and at a distance from each other. Depending on the application the number of the rollers in the belt conveyor may vary, being for example 2, 3-5 or 5-10. Preferably, both of the belt conveyors comprise a pair of rollers.

The operation of the medication dispenser is controlled with a control unit. The control unit may comprise a processor that is programmed to carry out the functions that are needed to operate the medication dispenser. The control unit may comprise a memory for storing, for example, the patient information.

The medication dispenser according to the invention reduces or even eliminates the risk of a medication package getting stuck inside the medication dispenser. Because a medication package is conveyed between the endless belts, the medication package may not get out of the conveying path to a space between the rollers. The medication dispenser according to the invention also enables to move a medication package in forward and backward directions easily and accurately.

A taking time of the medications contained in a medication package can be read from a label of the medication package or from a memory of the medication dispenser. The medication dispenser may comprise a reader arranged in connection with the conveying means for reading the taking time of the medications from the label of the medication package. The reader can be, for example, an optical reader, an RFID reader or an NFC reader. The optical reader, such as a camera, may be capable of reading text or a one- or two-dimensional bar code. The RFID and NFC readers are used to read RFID and NFC tags, respectively.

In a case where the medication packages are connected together to form a strip, the medication dispenser may comprise a cutter arranged in connection with the conveying means for separating the medication packages one by one from the strip. The cutter may also be arranged to open the medication package, whereby the medications can easily be taken out of the medication package.

According to an embodiment of the invention the diameter of the rollers of the belt conveyors is larger at the inlet end than at the outlet end of the first conveyor. By an inlet end of the first conveyor is meant the end that receives a medication package, and by an outlet end of the first conveyor is meant the end that feeds a medication package to the outlet. The larger diameter of the rollers at the inlet end facilitates the reception of a medication package. The smaller diameter of the rollers at the outlet end facilitates the feeding of a medication package to the outlet.

According to an embodiment of the invention the first conveyor is arranged to be turnable about an axis between a first and a second position, wherein at the first position the first conveyor is capable of receiving a medication package from a second conveyor of the conveying means. When receiving a medication package, the first conveyor is driven in the first conveying direction, so that the medication package that is fed to the inlet end of the first conveyor is conveyed towards the outlet end of the first conveyor. The first conveyor may be capable of conveying the medication package to the outlet at the first or the second position. Because the first conveyor is turnable about an axis, the first conveyor can convey the medication package to different locations. At the first position the medication package may be conveyed to a first location. At the second position the medication package may be conveyed to a second and a third location by changing the conveying more than two positions. The first conveyor is turned by means of an actuator, direction. In certain cases, the first conveyor may be arranged to be turnable between such as an electric motor.

The second conveyor, which conveys a medication package to the first conveyor, may receive the medication package from the first container, or from a third conveyor. In a case where the first container is provided with a strip of medication packages, the medication package is separated from the strip with a cutter before it is conveyed to the first conveyor.

According to an embodiment of the invention at the second position the first conveyor is capable of conveying the medication package to a second container of the medication dispenser. The medication package is conveyed to the second container when the patient has not taken the medication package during the allowable taking time. At the second position, the first conveyor is driven in the second conveying direction and the medication package is conveyed through the inlet end of the first conveyor to the second container. Alternatively, at the second position, the first conveyor is driven in the first conveying direction and the medication package is conveyed through the outlet end of the first conveyor to the second container.

According to an embodiment of the invention the distance between the belt conveyors is adaptive according to the thickness of the medication package. This allows conveying medication packages having varying thickness. Thickness of medication packages typically varies and is dependent on the amount and size of medications in the medication package. Adaptivity is needed to support different medication packages. A pair of conveyor parts in a fixed form can be made adaptive by using soft rollers with sufficient friction. Soft material gives when the medication package is conveyed between the conveyor parts. The conveyor parts can be tied to each other by using one or more springs. Pulling the medication package between the conveyor parts opens the conveyor. Spring force holds the medication package in control between the conveyor parts. It is also possible to use soft material in one pair of rollers inside the conveyor parts and springs on the other rollers. The conveyor spring structure requires less room because smaller hard rollers can be used instead of big soft rollers. The first conveyor may comprise a two-dimensional ball array, which enables two-dimensional adaptivity to the shape of the medication package.

According to an embodiment of the invention the belt conveyors are connected to each other using a plurality of springs. The springs are connected between the rollers of different belt conveyors. Preferably, a roller of a belt conveyor is connected at its both axle ends with springs to axle ends of another roller of another belt conveyor. The spring may be connected directly to an axle of a roller, or to a frame of a belt conveyor, to which frame the axle is attached. Preferably, the rollers of the inlet end are connected to each other with springs, and the rollers of the outlet end are connected to each other with springs. If soft rollers are used in the other end of the belt conveyers, springs can be used in the other end directly tying the different belt conveyer frames to each other.

According to an embodiment of the invention the medication dispenser comprises a first detector arranged in connection with the outlet for detecting the presence of a medication package at the outlet. The first detector can be, for example, an optical or magnetic detector. The presence of a medication package can easily be detected with an optical detector as the background differs from the package. The medication package can contain a separate tag, for example, a magnetic tag to be detected by a Hall sensor. As the medication package is being fed with the first conveyor to the outlet, the first detector provides information which can be utilised in positioning the medication package. After the medication package has been positioned, the first detector is used to detect the taking of the medication package from the outlet by the patient. Preferably, the first detector is arranged to detect the time of taking the medication package from the outlet.

According to an embodiment of the invention the medication dispenser comprises a second detector arranged below the first conveyor for detecting medication packages in the second container. The second detector can be, for example, an optical or magnetic detector. The purpose of the second detector is to give feedback about the container of missed medications, i.e. the second container. In different positions of the first conveyor, the second detector can give different information. In one position, the second detector can see the bottom of the second container and thus it can detect if the second container is empty or not. In another position, the second detector can detect if a medication package has dropped from the first conveyor to the second container, or if there is a possible overflow of the second container. In positions between, the second detector can detect how full the second container is.

According to an embodiment of the invention the medication dispenser comprises a third detector arranged above the first conveyor for monitoring the conveyance of medication packages. The third detector can be, for example, an optical or magnetic detector. As the medication package is being conveyed to the first conveyer, the third detector is arranged to give feedback information of the position of the medication package. The first and the third detector together make it possible to detect when the medication package is in the first conveyor and when the first conveyor can be safely turned.

According to an embodiment of the invention the outlet of the medication dispenser is provided with a lid. The lid is arranged to be open only during the time when the medication package is at the outlet. The lid is opened after the medication notification has been acknowledged. The lid is closed after the first detector has detected that the patient has taken the medication package from the outlet, or after the medication package has been retracted inside the medication dispenser.

The present invention also relates to a method for dispensing medications. A typical method according to the invention for dispensing medications using a medication dispenser according to the invention comprises setting a time window for the taking of medications contained in a medication package, and notifying a patient of the start of the time window. In a typical method according to the invention, if the patient acknowledges the notification before the end of the time window, the method comprises conveying the medication package to an outlet of the medication dispenser, and if the medication package is at the outlet after a predetermined time period, retracting the medication package inside the medication dispenser.

The method according to the invention enables to dispense medications to a patient in a controlled way at the safe taking time window. An idea of the invention is to allow the patient to take the medications at the right time, while limiting the time that the medications are physically available to the patient.

In the method according to the invention the medications are dispensed in medication packages by using the medication dispenser. The medication packages are inserted into a container of the medication dispenser by the patient or a caregiver of the patient, such as a nurse or a near relative. Each medication package contains medications to be taken at a prescribed time, i.e. at a taking time. The packages can be, for example, bags or mugs made of plastic, or blister packages made of plastic or metal foil. Typically, the medication packages are connected together to form a strip, from which medication packages are dispensed one package at a time according to the medical regimen of the patient. The medical regimen typically contains information about medications, their dosages and the taking times. The medication packages are arranged in the strip sequentially in time order.

In the method according to the invention a time window for the taking of medications contained in a medication package is first set. The time window defines the time during which the medication package may be conveyed to the outlet of the medication dispenser. The time window is set to contain at least the prescribed time for the taking of the medications contained in the medication package, i.e. the time window contains at least the taking time of the medications. The taking time may be obtained, for example, from a label of the medication package, or from a medical regimen stored in a memory of the medication dispenser. The time window may also contain time intervals preceding and following the taking time. This means that the starting time of the time window can be set to be earlier than that of the taking time, and the ending time of the time window can be set to be later than that of the taking time. However, in many cases the time window is set to correspond to the taking time.

When the time window defined for the medication package starts, the patient is notified that it is time to take the medications. The patient is typically notified with an audible signal through a loudspeaker of the medication dispenser. However, in some cases the patient may also be notified visually using a light source or a display of the medication dispenser. It is also possible to use a separate device, which can be, for example, a bracelet that contains a vibrator to notify the patient. In a case where the patient acknowledges the notification before the time window expires, the medication package is conveyed to the outlet from which the patient may take the medication package. The notification is acknowledged via a user interface of the medication dispenser. The user interface may comprise one or more buttons, and a display, such as a touch screen. The patient may acknowledge the notification, for example, by pressing a button or a certain icon that is shown on the touch screen. If the patient identification is required to be able to take the medication package from the medication dispenser, notification can be acknowledged with a patient specific RFID or NFC tag, magnetic key or electronic ID card. The medication dispenser may comprise an RFID, NFC or magnetic reader and/or an electronic card reader slot to support identification with a personal tag.

In a case where the medication package is still at the outlet after the predetermined time period, the medication package is retracted inside the medication dispenser. The presence of the medication package is monitored with a detector that is arranged in connection with the outlet. The predetermined time period defines the time during which the patient may take the medication package from the outlet. The length of the predetermined time period is typically a fraction of the length of the time window. The predetermined time can be, for example, less than 30 seconds, 30-60 seconds, 1-2 minutes, 2-5 minutes, 5-10 minutes, or 10-30 minutes.

According to an embodiment of the invention the method comprises, if the medication package has been retracted inside the medication dispenser, notifying the patient of the taking of the medications, and allowing the patient to acknowledge the notification. This means that the steps of conveying the medication package to the outlet and retracting the medication package inside the medication dispenser can be repeated one or more times until the time window ends, provided that the medication package has not been taken from the outlet. In a case where the patient has acknowledged the notification but for some reason not taken the medication package from the outlet during the predetermined time period, the patient thus has another possibility to take the medication package if he/she acknowledges the notification before the end of the time window.

According to an embodiment of the invention the method comprises, if the medication package is in the medication dispenser after the time window has ended, conveying the medication package to a second container of the medication dispenser. In a case where the patient has failed to acknowledge the notification, the medication package is kept within the medication dispenser during the time window, and after the time window has ended the medication package is conveyed to the second container, i.e. to a container of missed medications. In a case where the medication package has been conveyed to the outlet and then retracted from the outlet one or more times, the medication package may be in the medication dispenser at the time the time window ends, or a little later if the predetermined time period has not expired when the time window ends.

According to an embodiment of the invention the step of setting the time window for the taking of the medications contained in the medication package comprises reading a taking time of the medications from a label of the medication package, and selecting the time window to consist of the taking time, a first predetermined time interval preceding the taking time, and a second predetermined time interval following the taking time. The label of the medication package contains package-related information, such as the taking time of the medications. The information may be, for example, in a form of text, a one- or two-dimensional bar code, an RFID (radio frequency identification) or an NFC (near field communication) tag, or a magnetic tag. The taking time of the medications can be a certain time instant, such as 8:00 or 10:15, or a certain time interval, such as 8:00-10:00 or 10:15-11:00. The taking time of the medications can also be expressed vaguely, such as "in the morning", or "in the evening". In this case, the expressions "in the morning" and "in the evening" are defined as certain time intervals, such as 7:00-10:00 and 19:00-22:00, respectively. The first and the second predetermined time intervals define supplementary time for the taking of the medications. The length of the first and the second predetermined time interval can vary between the medication packages and can be dependent on the taking times of the previous medication packages. The length of the first and the second predetermined time interval can be, for example, less than 10 minutes, 10-30 minutes, 30-60 minutes, or 1-2 hours. According to an embodiment of the invention the length of the first and/or the second predetermined time interval is zero.

According to an embodiment of the invention the step of setting the time window for the taking of the medications contained in the medication package comprises reading a taking time of the medications from a memory of the medication dispenser, and selecting the time window to consist of the taking time, a first predetermined time interval preceding the taking time, and a second predetermined time interval following the taking time. The taking times of the medications are contained in the medical regimen of the patient.

According to an embodiment of the invention the method comprises detecting a time of taking the medication package from the outlet. The detected time can be used in defining a time window for the next medication package, e.g. the time can be used to prevent taking two consecutive medications too close to each other. The time when the patient takes the medication package from the outlet of the medication dispenser can be detected with a detector that is arranged in connection with the outlet.

According to an embodiment of the invention the method comprises changing the first and/or the second predetermined time interval based on the detected time of taking the medication package. For example, in a case where the medication package is taken from the outlet near the end of the time window, the first predetermined time interval can be decreased and the second predetermined time interval can be increased for the next medication package to be dispensed.

According to an embodiment of the invention the method comprises sending the detected time of taking the medication package over a communications network to a server. At the server, the detected times can be analysed and the results can be used to update the medical regimen of the patient. For example, if in the mornings medications are always taken delayed and the medications could be taken later, the taking time in the medical regimen can be adjusted to be more suitable for the patient.

According to an embodiment of the invention the method comprises reminding the patient of the taking of the medications. The patient can be reminded to acknowledge the notification and/or to take the medications from the outlet of the medication dispenser. The patient can be reminded with an audible signal through a loudspeaker of the medication dispenser. The patient may also be reminded visually using a light source or a display of the medication dispenser, or by a separate reminder device, which can be, for example, a bracelet that contains a vibrator to remind the patient.

According to an embodiment of the invention the patient is reminded at predefined intervals until the medication package has been taken from the outlet or the time window has ended. The patient can be reminded, for example, at intervals of 30 seconds, 1 minute or 2 minutes, or the interval can be changed e.g. continuously decreased during the time window. In a case where the patient has not taken the medications during the time window, a message can be sent over a communications network to the server. The server is preferably arranged to forward the message to the caregiver of the patient, such as a nurse or a near relative. The message typically contains the patient's name, a description of the detected problem to be solved, and the time of the observation.

The exemplary embodiments of the invention presented in this text are not interpreted to pose limitations to the applicability of the appended claims. The verb "to comprise" is used in this text as an open limitation that does not exclude the existence of also unrecited features. The features recited in the dependent claims are mutually freely combinable unless otherwise explicitly stated.

The exemplary embodiments presented in this text and their advantages relate by applicable parts to the medication dispenser as well as the method according to the invention, even though this is not always separately mentioned.

BRIEF DESCRIPTION OF THE DRAWINGS

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE DRAWINGS

Figure 1A:
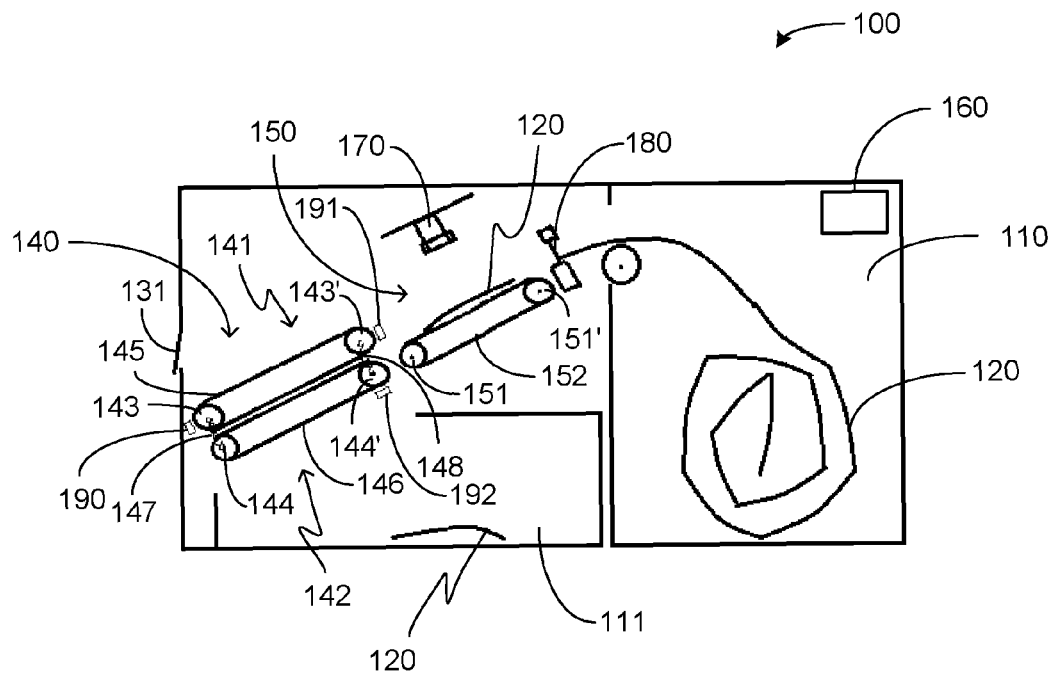
FIGS. 1a-1b illustrate a medication dispenser according to an embodiment of the invention.
Figure 1B:
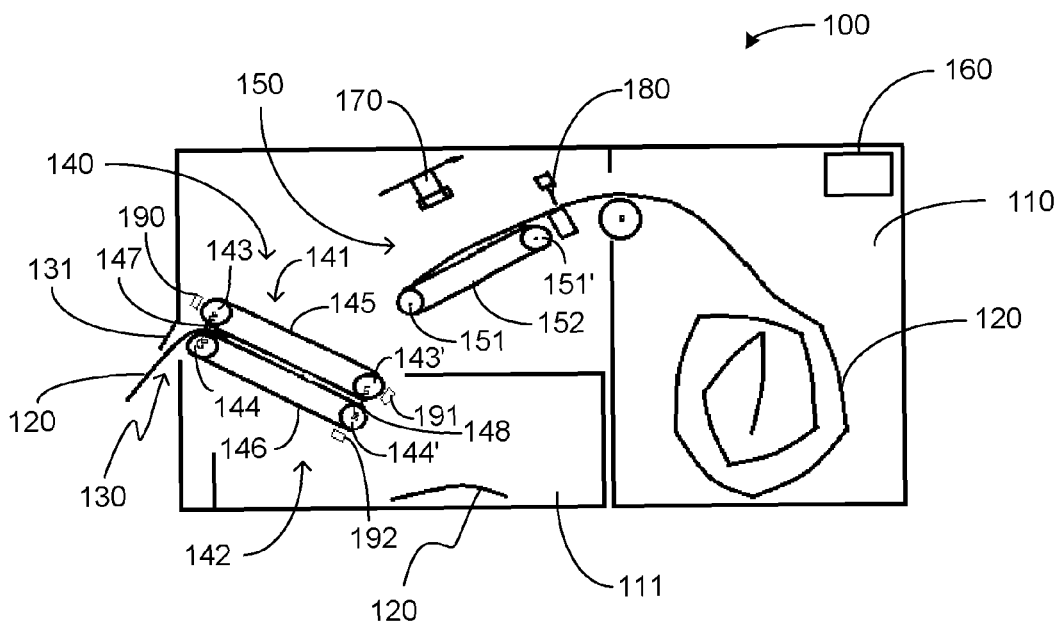

FIGS. 1a and 1b illustrate sectional views of a medication dispenser according to an embodiment of the invention. The medication dispenser 100 comprises a first container 110 for holding medication packages 120 to be dispensed. The medication packages 120 form a strip from which medication packages 120 are delivered one by one to a patient. The medication packages 120 are conveyed from the first container 110 to an outlet 130 of the medication dispenser 100 with a first and a second conveyor 140, 150. The first and the second conveyor 140, 150 are provided with integrated actuators (not shown) for operating the conveyors 140, 150. The operation of the medication dispenser 100 is controlled with a control unit 160.

The second conveyor 150 conveys medication packages 120 from the first container 110 to the first conveyor 140. The second conveyor 150 is a belt conveyor that comprises two rollers 151, 151' surrounded by an endless belt 152. At the second conveyor 150, the taking time of the medications is read from a label of the medication package 120 using a reader 170. The taking time is used in setting a time window that defines the time during which the medication package 120 may be conveyed to the outlet 130. After reading the label, the medication package 120 is separated from the strip by a cutter 180.

The first conveyor 140 comprises two opposing belt conveyors 141, 142 between which a medication package 120 is conveyed. Both of the belt conveyors 141, 142 comprise two rollers 143, 143', 144, 144' surrounded by an endless belt 145, 146. The belt conveyors 141, 142 are tied to each other with springs 147, 148. The belt conveyors 141, 142 can be rotated in both directions, whereby a medication package 120 between them may be conveyed in two opposite conveying directions.

The first conveyor 140 is turnable about an axis between a first and a second position. Referring to FIG. 1a, there is shown a situation where the first conveyor 140 is at the first position. At this position, the medication package 120 can be conveyed from the second conveyor 150 to the first conveyor 140.

Referring now to FIG. 1b, there is shown a situation where the first conveyor 140 is turned to the second position. Depending on the conveying direction of the first conveyor 140, the medication package 120 can be conveyed either to the outlet 130 or to a second container 111. In the situation of FIG. 1b, the patient has acknowledged the notification concerning the start of the time window, a lid 131 of the outlet has been opened and the medication package 120 has been conveyed to the outlet 130. The medication package 120 is held with the first conveyor 140 during the time the medication package 120 is kept at the outlet 130. In a case where the patient does not take the medication package 120 from the outlet 130 during the predetermined time period, the medication package 120 is retracted back inside the medication dispenser 100. In a case where the time window has not ended, the medication package 120 may be conveyed again to the outlet 130 if the patient acknowledges the notification another time. When the time window ends, and the patient has not taken the medication package 120, the medication package 120 is conveyed with the first conveyor 140 to the second container 111.

The medication dispenser 100 also comprises three detectors 190, 191, 192 for monitoring the conveyance of the medication packages 120 in the medication dispenser 100. The detectors 190, 191, 192 are attached in connection with the first conveyor 140.

Figure 2:
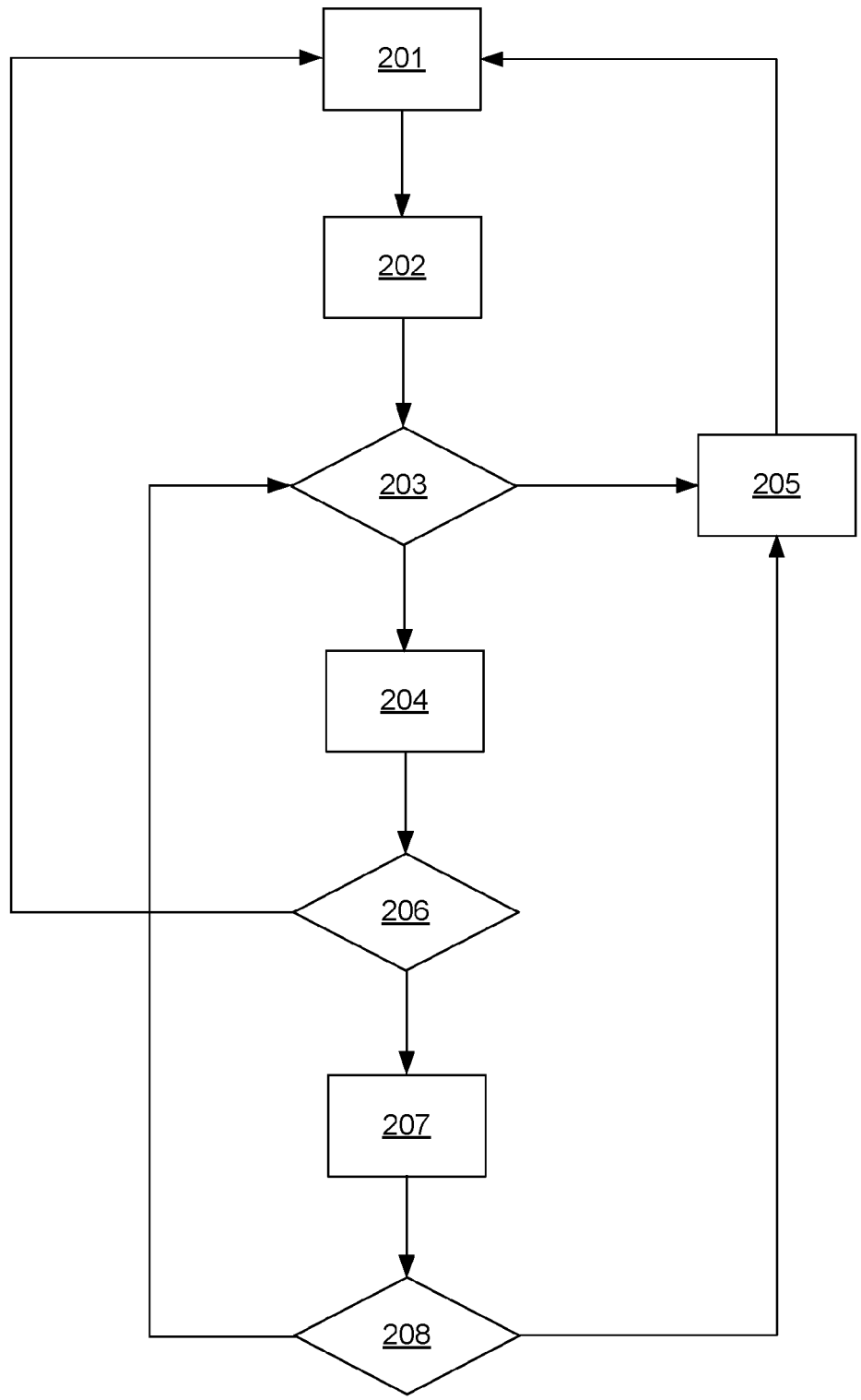
FIG. 2 illustrates a flow diagram of a method according to an embodiment of the invention.

FIG. 2 illustrates a flow diagram of a method according to an embodiment of the invention for dispensing medications.

At step 201 a time window for the taking of medications contained in a medication package is set. The time window defines the time during which the medication package may be conveyed to the outlet of the medication dispenser.

At step 202 the patient is notified of the start of the time window.

At step 203 it is waited for the patient to acknowledge the notification during the time window. If the patient acknowledges the notification before the end of the time window, the medication package is conveyed to the outlet of the medication dispenser (step 204). Otherwise, the medication package is conveyed to the container of missed medications (step 205), and then the method is continued at step 201.

At step 206 it is waited for the patient to take the medication package from the outlet. If the patient takes the medication package from the outlet during the predetermined time period, the method is continued at step 201. However, if the medication package is at the outlet after the predetermined time period the medication package is retracted inside the medication dispenser (step 207).

At step 208 it is determined whether the time window has ended or not. If the time window has ended the medication package is conveyed to the container of missed medications (step 205), and then the method is continued at step 201. If the time window has not ended, the method is continued at step 203, whereby the patient is given another possibility of taking the medications contained in the medication package.

Only advantageous exemplary embodiments of the invention are described in the figures. It is clear to a person skilled in the art that the invention is not restricted only to the examples presented above, but the invention may vary within the limits of the claims presented hereafter. Some possible embodiments of the invention are described in the dependent claims, and they are not to be considered to restrict the scope of protection of the invention as such.

The invention claimed is:

1. A medication dispenser, comprising:
    a first container for holding medication packages to be dispensed, and
    conveying means for conveying medication packages from the first container to an outlet of the medication dispenser, the conveying means comprising a first conveyor arranged in connection with the outlet and being capable of conveying a medication package in a first and a second conveying direction, so that a medication package can be conveyed to the outlet and retracted inside the medication dispenser;
    wherein the first conveyor comprises two opposing belt conveyors between which a medication package is arranged to be conveyed, both of the belt conveyors comprising an endless belt and a plurality of rollers around which the endless belt is arranged, and wherein the first conveyor is arranged to be turnable about an axis between a first and a second position, wherein at the first position the first conveyor is capable of receiving a medication package from a second conveyor of the conveying means.

2. The medication dispenser according to claim 1, wherein a diameter of the rollers of the belt conveyors is larger at the inlet end than at the outlet end of the first conveyor.

3. The medication dispenser according to claim 1, wherein at the second position the first conveyor is capable of conveying the medication package to a second container of the medication dispenser.

4. The medication dispenser according to claim 1, wherein a distance between the belt conveyors is adaptive according to the thickness of the medication package.

5. The medication dispenser according to claim 1, wherein the belt conveyors are connected to each other using a plurality of springs.

6. The medication dispenser according to claim 1, wherein the medication dispenser comprises a first detector arranged in connection with the outlet for detecting the presence of a medication package at the outlet.

7. The medication dispenser according to claim 1, wherein the medication dispenser comprises a second detector arranged below the first conveyor for detecting medication packages in the second container.

8. The medication dispenser according to claim 1, wherein the medication dispenser comprises a third detector arranged above the first conveyor for monitoring the conveyance of medication packages.

9. The medication dispenser according to claim 1, wherein the medication dispenser comprises a reader arranged in connection with the conveying means for reading the taking time of medications from a label of a medication package.

10. A method for dispensing medications using a medication dispenser, said medication dispenser comprising:
   a first container for holding medication packages to be dispensed, and
   conveying means for conveying medication packages from the first container to an outlet of the medication dispenser, the conveying means comprising a first conveyor arranged in connection with the outlet and being capable of conveying a medication package in a first and a second conveying direction, so that a medication package can be conveyed to the outlet and retracted inside the medication dispenser;

wherein the first conveyor comprises two opposing belt conveyors between which a medication package is arranged to be conveyed, both of the belt conveyors comprising an endless belt and a plurality of rollers around which the endless belt is arranged, wherein the first conveyor is arranged to be turnable about an axis between a first and a second position, wherein at the first position the first conveyor is capable of receiving a medication package from a second conveyor of the conveying means, and wherein the method comprises:
   setting a time window for the taking of medications contained in a medication package,
   notifying a patient of the start of the time window, and
   if the patient acknowledges the notification before the end of the time window:
      conveying the medication package to an outlet of the medication dispenser, and
      if the medication package is at the outlet after a predetermined time period, retracting the medication package inside the medication dispenser.

11. The method according to claim 10, wherein the method comprises, if the medication package is in the medication dispenser after the time window has ended, conveying the medication package to a second container of the medication dispenser.

12. The method according to claim 10, wherein the step of setting the time window for the taking of the medications contained in the medication package comprises:
   reading a taking time of the medications from a label of the medication package, and
   selecting the time window to consist of the taking time, a first predetermined time interval preceding the taking time, and a second predetermined time interval following the taking time.

13. The method according to claim 10, wherein the method comprises detecting a time of taking the medication package from the outlet.

14. The method according to claim 13, wherein the method comprises changing the first and/or the second predetermined time interval based on the detected time of taking the medication package.

* * * * *